United States Patent
Wang et al.

(10) Patent No.: US 10,975,418 B1
(45) Date of Patent: Apr. 13, 2021

(54) RAPID PCR-BASED VIRUS DETECTION METHOD, AND KITS THEREFOR

(71) Applicant: JIANGSU COWIN BIOTECH CO., LTD, Taizhou (CN)

(72) Inventors: Chunxiang Wang, Taizhou (CN); Jinhai Guo, Taizhou (CN); Huanhuan Xiao, Taizhou (CN)

(73) Assignee: JIANGSU COWIN BIOTECH CO., LTD, Taizhou (CN)

( * ) Notice: Subject to any disclaimer, the term of this patent is extended or adjusted under 35 U.S.C. 154(b) by 0 days.

(21) Appl. No.: 16/984,927

(22) Filed: Aug. 4, 2020

Related U.S. Application Data

(63) Continuation of application No. PCT/CN2020/098691, filed on Jun. 29, 2020.

(51) Int. Cl.
*C12Q 1/6806* (2018.01)
*C12Q 1/70* (2006.01)
*C12Q 1/6851* (2018.01)

(52) U.S. Cl.
CPC ......... *C12Q 1/6806* (2013.01); *C12Q 1/6851* (2013.01); *C12Q 1/70* (2013.01)

(58) Field of Classification Search
CPC ....... C12Q 1/6806; C12Q 1/6851; C12Q 1/70
See application file for complete search history.

(56) References Cited

U.S. PATENT DOCUMENTS 6,294,365 B1 * 9/2001 De Rosier .............. C12N 9/127
435/188

FOREIGN PATENT DOCUMENTS

RU 2694499 C1 * 7/2019

OTHER PUBLICATIONS

Cobas SARS-CoV2., https://www.who.int/diagnostics_laboratory/eul_0504-046-00_cobas_sars_cov2_qualitative_assay_ifu.pdf?ua=1m pp. 1-31, March 2020.*
Li et al., International Journal of Infectious Diseases, 85, 85: 167-174, Jan. 2019.*

* cited by examiner

*Primary Examiner* — Cynthia B Wilder
(74) *Attorney, Agent, or Firm* — Lin Sun-Hoffman; Yong Chen; Liu Chen & Hoffman LLP

(57) ABSTRACT

The present invention provides a rapid and high-sensitivity method to detect virus by qPCR nucleic acid amplification. A viral sample containing a RNA virus such as a corona virus is mixed with a virus preservation solution and a nucleic acid amplification reaction preparation (which can be in a lyophilized powder) to prepare the PCR-sample solution. The virus preservation solution can preserve the viral sample and prevent RNA degradation at room temperature for an extended period of time. No viral nucleic acid extraction step is needed.

19 Claims, No Drawings
Specification includes a Sequence Listing.

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ccctgtgggt tttacactta a                                              21

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
acgattgtgc atcagctga                                                 19

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
ccgtctgcgg tatgtggaaa ggttatgg                                       28

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ggggaacttc tcctgctaga at                                             22

<210> SEQ ID NO 5

```
<211> LENGTH: 22
<212> TYPE: DNA
<213> ORGANISM: Artificial Sequence
<220> FEATURE:
<223> OTHER INFORMATION: Synthetic

<400> SEQUENCE: 5
cagacatttt gctctcaagc tg                                               22

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ttgctgctgc ttgacagatt                                                  20

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
ccatcctgcg tctggacct                                                   19

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ccgtggtggt gaagctgtag                                                  20

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
actacctcat gaagatcct                                                   19
```

RAPID PCR-BASED VIRUS DETECTION METHOD, AND KITS THEREFOR

CROSS REFERENCE TO RELATED APPLICATION

This application is a continuation of International Application No. PCT/CN2020/098691 filed on Jun. 29, 2020, the disclosure of which is incorporated herein by reference in its entirety.

INCORPORATION OF SEQUENCE LISTING

This application includes a Sequence Listing which has been submitted in ASCII format via EFS-Web, named "CWN001US_ST25.txt," which is 2 KB in size and created on Aug. 3, 2020. The contents of the Sequence Listing are incorporated herein by reference in their entirety.

TECHNICAL FIELD

The invention relates to the field of molecular biology, in particular to a virus preservation solution, a nucleic acid amplification reaction solution, a nucleic acid PCR amplification method, and a PCR amplification kit.

BACKGROUND

Currently, common viral RNA detection methods usually include three steps: 1) collecting viral samples from subjects and transferring the samples to a lab; 2) extracting viral RNA from the viral samples by silica gel membrane column or magnetic bead adsorption; 3) performing RT-PCR and using fluorescence quantitative detection (the results can be interpreted based on the Ct value).

In such methods, the RNA extraction kit is usually separate from the viral sample preservation kit, as is the RT-qPCR detection kit. Also, the collected sample often contain RT-PCR polymerase inhibitors which would hinder the nucleic acid amplification if directly mixed with the PCR reagents. In addition, the preservation solution usually requires a storage and transportation condition at 2-8° C., and the common RT-qPCR detection kits are liquid preparations which need to be stored at −20 degrees and transported in refrigerated condition (such as with dry ice). The extraction and PCR process requires stringent biosafety standards as well as experience and skill of the lab technicians. The final assay results are usually obtained in the order of many hours.

Overall, the above traditional detection methods are cumbersome, complex and prone to error. Their low efficiency can severely limit the response speed and effectiveness of the society to emergency situation, such as the breakout of the SARS-CoV-2 virus, and can lead to undesired delay in isolating and treating infected patients.

There is a need for improved and simplified compositions, kits, and methods for viral RNA preservation, extraction, and detection with good efficiency and reduced probability of error.

SUMMARY

The present disclosure provides a virus preservation solution, a nucleic acid amplification reaction preparation (which can be in a lyophilized powder), a qPCR-based method to detect virus by nucleic acid amplification using the virus preservation solution and the nucleic acid amplification reaction preparation, and a PCR kit including the virus preservation solution and the nucleic acid amplification reaction preparation. The virus preservation solution can preserve a viral sample and prevent RNA degradation at room temperature for an extended period of time. The virus preservation solution is suitable to preserve a viral sample containing a RNA virus, such as a coronavirus, more particularly SARS-CoV-2 virus. The sample solution can be directly combined with the nucleic acid amplification reaction preparation without any viral nucleic acid extraction step for qPCR amplification for rapid and high-sensitivity virus detection.

In one aspect, there is provided a virus preservation solution which comprises bovine serum albumin (BSA), fish gelatin, a surfactant, a pH buffer, and wherein the virus preservation solution has a pH in the range of between 8.0 to 8.5, for example, pH 8.0. The pH buffer can comprise Tris-HCl. In some embodiments, the virus preservation solution can further include at least one or both of KCl or $MgCl_2$. In some embodiments, the virus preservation solution can further include at least one or both of dimethyl sulfoxide (DMSO) and glycerol. The virus preservation solution can also further include inhibitors that suppress the inhibitors of Taq polymerase in PCR reaction.

In some embodiments of the virus preservation solution, the pH buffer comprises Tris-HCl, and in the total amount of the solution, the molar concentration of Tris-HCl is between 10 mM and 200 mM, the weight concentration of BSA is between 1 μg/μl and 10 μg/μl, and the weight percentage of fish gelatin is between 0.1% and 2%. In some of these embodiments, the virus preservation solution further comprises KCl, $MgCl_2$, DMSO and glycerol, and wherein in the total amount of the solution, the molar concentration of KCl is between 10 mM and 200 mM, the molar concentration of $MgCl_2$ is between 1.5 and 6 mM, the volume percentage of DMSO is between 0.1% and 5%, and the volume percentage of glycerol is between 1% and 10%.

In another aspect, there is provided a nucleic acid amplification reaction solution which comprises M-MLV Reverse Transcriptase (MMLV), Taq DNA polymerase, dNTP, primers and fluorescence probes. The nucleic acid amplification reaction solution can further comprise KCl and/or $MgCl_2$, a pH buffer such as Tris-HCl to maintain the pH of the solution at about pH 8.0-8.5. The nucleic acid amplification reaction solution can further comprise polyoxyethylene (20) sorbitan monolaurate.

There is also provided a lyophilized powder prepared by lyophilizing the nucleic acid amplification reaction solution(s) described herein. To obtain such lyophilized powder, the nucleic acid amplification reaction can be first added a lyoprotectant, such as a sugar and/or PEG6000.

In a further aspect, there is provided a method of preparing a viral sample for PCR amplification. The method includes adding a first mixture of a viral sample with a virus preservation solution described herein to a nucleic acid amplification reaction solution described herein or the lyophilized powder prepared by lyophilizing the nucleic acid amplification reaction solution, to thereby obtain a PCR-sample solution. When the virus is an RNA virus, preferably a coronavirus, more preferably SARS-CoV-2 virus, the method can further include performing qPCR on the PCR-sample solution. The thermocycling conditions for the qPCR include: reverse transcription reaction: 45° C.-60° C., preferably 50° C.-55° C., for 0.5 min-10 min, preferably 0.5 min-1 min; thermal denaturation reaction: 94° C.-99° C. for 1 s-60 s; amplification reaction: 94° C.-99° C. for 2 s-5 s, 55°

C.-60° C. for 10 s-45 s, preferably 10 s-30 s, for multiple cycles, preferably at least 35 cycles, or at least 40 cycles.

In yet a further aspect, a PCR amplification kit is provided, which comprises a virus preservation solution as described herein stored in a first container (such as a vial), and a nucleic acid amplification reaction preparation (solution, or preferably lyophilized powder), as described herein, in a second container. For detecting a coronavirus, such as SARS-CoV-2 virus, the nucleic acid amplification reaction preparation can include primers and probes suitable for its amplification and detection. The kit can further include a positive control containing a known nucleic acid comprising a sequence characteristic of the target, and a negative control containing a known nucleic acid not comprising a sequence characteristic of the target.

DETAILED DESCRIPTION OF EXAMPLE EMBODIMENTS

The present invention provides viral nucleic acid preservation solution, nucleic acid amplification reaction preparation, kits containing the viral nucleic acid preservation solution and nucleic acid amplification reaction preparation, and associated methods for preparing and performing PCR amplification on the nucleic acid of the virus, which allow for rapid, high-sensitivity, and accurate detection of viral infection of human subjects.

As described herein, all the solutions (virus preservation solutions, and nucleic acid amplification reaction solutions) of the present disclosure are water-based, meaning that besides the components explicitly provided or mentioned, the remaining balance is water. In all compositions (solutions, lyophilized powders) described herein, the amount/concentration/percentage of any components of the compositions refers to the final amount/concentration/percentage of the components in the total compositions.

In one aspect, the present disclosure provides a virus preservation solution, which comprises a pH buffer, bovine serum albumin (BSA), fish gelatin, and a surfactant, and wherein the virus preservation solution has a pH in the range of between 8.0 to 8.5, for example, at about 8.0.

In some embodiments of the virus preservation solution, the weight concentration of BSA can be 1-10 µg/µl, e.g., 1-5 µg/µl, and the weight percentage of fish gelatin can be 0.1%-2%, e.g., 0.1%-1%.

The pH buffer can comprise Tris-HCl buffer, which can be in the amount of 10 mM-200 mM in the total virus preservation solution.

In some embodiments, the virus preservation solution can further include potassium chloride and/or magnesium chloride. $MgCl_2$ can control the activity of DNA polymerase and the melting temperature of DNA double-strand, and can have a significant impact on the specificity of the PC R reaction and the product. KCl and/or $MgCl_2$ can also be included in the nucleic acid amplification reaction preparation, as will be described below. In the virus preservation solution, the molar concentration of KCl can be 10 mM-100 mM, and the molar concentration of $MgCl_2$ can be 1.5 mM-6 mM. In some embodiments, the virus preservation solution can further include a preservative such as sodium azide ($NaN_3$), thimerosal, antibiotics, biocides such as proclin300, etc., which can suppress the growth of bacteria, and/or one or more chelating agents such as EDTA, CDTA, HEDTA, EGTA and EDDA, etc., which can protect RNA from degradation. In some embodiments, the concentration of $NaN_3$ can be 0.01-0.1% (w/v) of the solution. In some embodiments, the concentration of EDTA can be 0.1-5 mM.

In some embodiments, the virus preservation solution can further include DMSO and/or glycerol. DMSO and glycerol can promote the opening of nucleic acid secondary structure, especially suitable for amplifying templates with high GC content and complex secondary structure. The volume percentage of DMSO can be 0.1%-5%. The volume percentage of glycerol can be 1%-10%.

In some embodiments, the virus preservation solution can further include agents for deactivating or reducing the inhibitory effect of polymerase inhibitors which may be present in the viral sample, for example, T4 gp32 protein, spermidine, PEG6000, etc.

In some embodiments, the surfactant can comprise one or more of sodium dodecyl sulfate (SDS), polyoxyethylene (20) sorbitan monolaurate (Tween 20), NP-40 (CAS Registry Number 9016-45-9), and Triton-100 (CAS Number: 9002-93-1). In some embodiments, these surfactants can each have a concentration of 0.01-0.1% (w/v).

In some embodiments, the virus preservation solution can comprise the following components (in the total amount of the solution): Tris-HCl, 10-200 mM; DMSO (v/v), 0.1%-5%; glycerol (v/v), 1%-10%; BSA, 1-10 µg/µl; fish gelatin is 0.1%-2% (w/w).

In another aspect, the present disclosure provides a nucleic acid amplification reaction solution, which includes M-MLV Reverse Transcriptase (MMLV), Taq DNA polymerase, dNTP, PCR primers suitable for amplifying target nucleic acids, and fluorescence probes suitable for qPCR detection.

MMLV in the nucleic acid amplification reaction solution is used to reverse transcribe RNA into cDNA. An MMLV which has strong resistance to inhibitors can be used to speed up the reverse transcription reaction. Taq DNA polymerase is used for the synthesis of DNA strands in the 5' to 3' direction guided by the target sequence as a template and specifically paired with primers. Preferably, an antibody-modified Taq DNA polymerase activatable only at high temperature is used.

In some embodiments, the nucleic acid amplification reaction solution can further comprise both KCl and $MgCl_2$. In one embodiment, the concentration of KCl in the nucleic acid amplification reaction solution can be 10-200 mM.

In some embodiments, particularly if the nucleic acid amplification reaction solution may be later lyophilized to prepare lyophilized powder form, the solution may include a sugar (e.g., trehalose, sucrose). The sugar can protect the reverse transcriptase and Taq DNA polymerase against denaturation or other loss of function during lyophilization (described below), and can improve the thermal stability and activity of the enzymes.

In some embodiments, the nucleic acid amplification reaction solution can include other lyoprotectants such as polyvinylpyrrolidone (PVP), mannitol, sorbitol, lecithin, and sodium thiosulfate.

In some embodiments, the nucleic acid amplification reaction solution can further include polyoxyethylene (20) sorbitan monolaurate (TWEEN-20).

In some embodiments, the nucleic acid amplification reaction solution can include the following components: MMLV, 1-50 U/µl; Taq DNA polymerase, 0.1-3 U/µl; KCl, 10-200 mM; dNTP, 0.05-0.5 mM; primers 0.05-0.5 µM; probes 0.05-0.5 µM. In some embodiments, the nucleic acid amplification reaction solution can also include a sugar, e.g., trehalose and/or sucrose, and polyoxyethylene (20) sorbitan monolaurate. For example, the weight concentration of trehalose can be between 1% and 10%, the weight concentration of sucrose can be between 1% and 10%, and the weight concentration of polyoxyethylene (20) sorbitan monolaurate is between 0.005% and 0.2%.

The amount/concentration described herein for the nucleic acid amplification reaction solution refers to the amount/concentration of these components after the solution has been mixed with predetermined amount of virus preservation solution (containing viral sample) and ready for qPCR amplification. As used herein, one unit (U) Taq DNA Polymerase is defined as the amount of enzyme that incorporates 10 nmol of total deoxyribonucleoside triphosphates into acid precipitable DNA within 60 min at +65° C. One unit (U) of MMLV incorporates 1 nmol of dTTP in 10 min at 37° C. using 200-400 micromolar oligo dT-primed poly (A) as template.

The primers and fluorescent probes in the nucleic acid amplification reaction solution can be designed or selected based on the nucleic acid of the virus. For example, for SARS-CoV-2 virus, primer sequences based on ORF1ab, and/or nucleocapsid protein gene (N gene) can be used.

For ease of storage and transportation, the nucleic acid amplification reaction solution as described herein can be lyophilized to obtain a preparation in lyophilized powder form. Such lyophilized powder form of the nucleic acid amplification reaction preparation can be stored and transported at room temperature while maintaining good stability without any significant degradation or drop in efficacy for an extended time (e.g., at least six months).

Collectively, the nucleic acid amplification reaction solution and its lyophilized powder form are referred to as nucleic acid amplification reaction preparation.

In a further aspect, the present disclosure provides a method for preparing a viral sample for PCR amplification. A viral sample can be mixed with the virus preservation solution and the nucleic acid amplification reaction preparation as described herein, and without further extraction or other treatment step, placed in an appropriate reaction plate/container suitable for qPCR instrument for amplification. The combined effect of the virus preservation solution and the nucleic acid amplification reaction preparation can enable the amplification reaction to be completed within 30 minutes, e.g., in as little as 15 minutes. This is a dramatic shortening of time for virus detection and can have a significant impact on the societal response strategy for viral infection control in a pandemic where speedy diagnosis plays a key role.

In operation, the mixing can be done sequentially or simultaneously. For example, a viral sample can be collected from a subject with a pharyngeal swab, and the swab can be immersed in the virus preservation solution, mixed by shaking, and then this virus preservation solution (loaded with the viral sample) is mixed with the nucleic acid amplification reaction preparation. The viral sample can also be first saved in another traditional virus collection solution, e.g., Hanks balanced salt solution, or saline, and subsequently, the collection solution is mixed with the virus preservation solution of the present invention, and then mixed with the nucleic acid amplification reaction preparation. The method can also include performing PCR amplification for the mixed solution containing the sample on a qPCR (or real-time PCR) instrument, e.g., Applied Biosystems 7500 Real-Time PCR system (ABI 7500).

In a further aspect, the present disclosure provides a kit for preserving and amplifying viral nucleic acid. The kit comprises a virus preservation solution as described herein stored in a first container (such as a vial), and a nucleic acid amplification reaction preparation (solution, or preferably lyophilized powder), as described herein, in a second container. The kit can further include a positive control containing a known nucleic acid comprising a sequence characteristic of the target, and a negative control containing a known nucleic acid not comprising a sequence characteristic of the target.

The compositions, solutions, kits and methods of the present disclosure are particularly suitable for detecting an RNA virus, preferably a coronavirus, more preferably SARS-CoV-2 virus. For example, the thermocycling conditions for the qPCR amplification of an RNA virus can be as follows:

reverse transcription: 45° C.-60° C. (e.g., 50° C.-55° C.) for 0.5 min-10 min (preferably, for expediting the experiment, 0.5 min-1 min).

thermal denaturation: 94° C.-99° C. for 10 s-60 s (for example, at 98° C. for 10 s);

amplification reaction: 94° C.-99° C. for 1 s-10 s (for example, 98° C. for 1 s), 55° C.-60° C. for 10 s-45 s (e.g., 58° C. for 15 s-30 s) for multiple cycles (e.g., at least 30 cycles, typically 40 to 45 cycles)

The entire PCR amplification process can be completed in as little as 20-30 minutes, and in some instances, 15 minutes or less.

EXAMPLES

Example 1: Comparison of Different Virus Preservation Solutions

IBV virus (chicken infectious bronchitis virus, a coronavirus) was used as a reference sample, and different dilutions of IBV virus are stored in different virus preservation solutions, and then these samples are each divided into two: one is used for direct PCR detection, and for each second portion viral RNA was first extracted and then PCR detection were performed on the extracted RNA. The effect and sensitivity of different preservation solutions are compared.
Material:

The following preservation solutions were tested and compared:

Preservation solution A: NaOH (20 mmol/L), Surfactin (0.5% [w/v]), DMSO (5%[v/v]); sucrose (8%[w/v]), Chelex-100 (0.9%, [w/v]).

Preservation solution B: β-mercaptoethanol (10 mmol/L-15 mmol/L), 8-hydroxyquinoline (0.05 mol/L-0.1 mol/L, sodium acetate (2 mol/L-5 mol/L), sodium dodecyl sarcosine (5%-10% [w/v]), guanidine isothiocyanate (10%-15% [w/v]), Tris HCl (0.01 mol/L-0.05 mol/L), EDTA (0.01 mol/L-0.05 mol/L), triton-100 (0.1%-0.5% [v/v]), glycerol (3%-8% [v/v]), sodium azide (0.08%-0.1%[w/v]).

Preservation solution C: an example solution (pH 8.0) according to the present disclosure, in particular:

TABLE 1

| | |
|---|---|
| Tris.HCl | 50 mM |
| KCl (2M) | 25 mM |
| DMSO | 1% (v/v) |
| Glycerol | 2% (v/v) |
| BSA | 5 µg/µl |
| Fish gelatin | 0.1% (w/w) |

A number of simulated preservation solutions are also used for comparison purpose, which include 1×PBS (10 mM); ½×PBS, obtained by diluting the 1×PBS 2-fold; and ¼×PBS, obtained by diluting the 1×PBS 4-fold.

Procedure:

IBV virus was obtained and diluted to $1\times10^8$ copies/ml as the stock solution. Then the following series of solutions were prepared by diluting the stock solution at different dilution factors: $1\times10^7$, $1\times10^6$, $1\times10^5$, $1\times10^4$, $1\times10^3$, $1\times10^2$ copies/ml, which were used as the templates for direct amplification (without RNA extraction step). Also, 200 µl of solutions at each dilution level was taken to extract RNA (elute with 50 µL RNA free water, and PCR reaction inhibitor are removed compared to the direct amplification), which were then used as a non-direct amplification templates.

IBV virus specific primers/probes were used for PCR detection.

Reagents for direct amplification are summarized in the following table.

TABLE 2

| Components | Amounts (total 50 µL) |
|---|---|
| 4xonestep TaqMan Buffer | 12.5 |
| dNTP ( 10 mM ) | 2 |
| IBV primer/probe ( 10 µM ) | 2 |
| Taq Polymerase ( 5U/µl ) | 1 |
| MMLV ( 200U/µl ) | 2 |
| Templates | 30.5 |

Reagents for amplification with the RNA extraction step (or two-step) are shown in the below table:

TABLE 3

| Components | Amounts (total 50 µL) |
|---|---|
| 4xonestep TaqMan Buffer | 12.5 |
| dNTP ( 10 mM ) | 2 |
| Taq Polymerase ( 5U/µl ) | 1 |
| MMLV ( 200U/µl ) | 2 |
| IBV primer/probe ( 10 µM ) | 2 |
| Templates | 8 |
| ddH$_2$O | 22.5 |

PCR thermocycling conditions used:

TABLE 4

| Reverse transcription | 55° C. | 1 min | |
| --- | --- | --- | --- |
| Denaturation | 95° C. | 20 s | |
| Extension and fluorescence reading | 95° C. | 5 s | 45 cycles |
| | 58° C. | 30 s | |

On the software interface of ABI 7500, set threshold to 10000, baseline to 6-20 cycles. The results (Ct values) are shown in the below table.

TABLE 5

| IBV concentration | | $10^7$ | $10^6$ | $10^5$ | $10^4$ | $10^3$ | $10^2$ |
|---|---|---|---|---|---|---|---|
| Solution A | Direct | 27.29 | 32.85 | 37.57 | N/A | N/A | N/A |
| | Two-step | 22.41 | 26.25 | 28.93 | 32.52 | 34.94 | N/A |
| Solution B | Direct | 26.98 | 30.92 | 33.2 | 36.37 | N/A | N/A |
| | Two-step | 22.37 | 26.16 | 29.33 | 34.21 | 36.93 | 39.7 |
| Solution C | Direct | 20.65 | 24.08 | 28.28 | 32.44 | 36.22 | 39.97 |
| | Two-step | 23.95 | 26.92 | 29.58 | 32.59 | 34.99 | 38.15 |
| 1 × PBS | Direct | N/A | N/A | N/A | N/A | N/A | N/A |
| | Two-step | 25.21 | 26.42 | 29.67 | 33.35 | 37.65 | N/A |
| ½ × PBS | Direct | 29.18 | 32.46 | 35.85 | 38.94 | N/A | N/A |
| | Two-step | 23.88 | 26.19 | 29.49 | 31.91 | 37.59 | N/A |
| ¼ × PBS | Direct | 27.54 | 31.11 | 34.93 | 39.36 | N/A | N/A |
| | Two-step | 23.47 | 27.19 | 29.87 | 31.89 | 37.6 | 38.76 |

Results

From these experimental results, it can be seen that the virus preservation solution of the present invention (solution C) can be used for direct amplification detection, and the sensitivity is even higher than that of the non-direct amplification group (where extracted RNA was used as the template). Further, among the different formulations compared, the virus preservation solution of the present invention has the best preservation effect on viral nucleic acid than other preservation solutions. For direct amplification, Ct values of preservation solution C is about 6-7 lower than those of preservation solutions A and B, equivalent to 64-128 times higher sensitivity.

Example 2: Viral Nucleic Acid Detection Kit and qPCR Amplification

This example provides a novel coronavirus (SARS-CoV-2) sample amplification nucleic acid detection kit, which includes: (1) SARS-CoV-2 preservation solution, (2) SARS-CoV-2 PCR amplification reaction lyophilized powder, (3) positive control; and (4) negative control.

Preparations of Components:

(1) SARS-CoV-2 preservation solution (pH 8.0) are prepared according to the below table:

TABLE 6

| Reagents | Final Conc. |
|---|---|
| NaOH | 10-200 mM |
| Tris.HCl | 10-200 mM |
| KCl (2M) | 10-100 mM |
| MgCl$_2$ (1M) | 1.5-6 mM |
| DMSO | 1-5% (v/v) |
| Glycerol | 1-10% (v/v) |
| BSA | 1-5 ug/ul |
| Fish gelatin | 0.1-1% (w/w) |

(2) SARS-CoV-2 nucleic acid amplification reaction lyophilized powder:

Primers and probes were designed based on the RNA sequence of SARS-CoV-2 virus ORF1ab and N genes, where ORF1ab-F: 5'-CCCTGTGGGTTTTACACTTAA-3' (SEQ ID No. 1), ORF1ab-R: 5'-ACGATTGTG-CATCAGCTGA-3' (SEQ ID No. 2), ORF1ab-P: 5'-FAM-CCGTCTGCGGTATGTGGAAAGGTTATGG-BHQ1-3' (SEQ ID No. 3); N-F: 5'-GGG-GAACTTCTCCTGCTAGAAT-3' (SEQ ID No. 4); N-R: 5'-CAGACATTTTGCTCTCAAGCTG-3' (SEQ ID No. 5); N-P: 5'-ROX-TTGCTGCTGCTTGACAGATT-BHQ2-3' (SEQ ID No. 6). The human ACTB gene is used as an internal reference gene, and the primer probe sequence is ACTB-F: 5'-CCATCCTGCGTCTGGACCT-3' (SEQ ID No. 7), ACTB-R: 5'-CCGTGGTGGTGAAGCTGTAG-3' (SEQ ID No. 8), ACTB-P: 5'-VIC-ACTACCTCATGAA-GATCCT-MGB-3' (SEQ ID No. 9).

A solution of 25 μL (pH 8.0) was prepared according to the recipe shown in the below table:

TABLE 7

| | |
|---|---|
| MMLV | 2-50 U/μl |
| Taq polymerase | 0.05-1 U/μl |
| Tris.HCl | 10-200 mM |
| KCl (2M) | 10-100 mM |
| Trehalose (w/w) | 1%-10% |
| Sucrose (w/w) | 1%-10% |
| PEG6000 (w/w) | 1%-5% |
| Tween-20 (w/w) | 0.005%-0.2% |
| Primer | 200 nM |
| Probe | 100 nM |

Then the solution was lyophilized using a freeze-dryer to obtain the lyophilized powder.

(3) SARS-CoV-2 positive control:

This positive control was obtained as a mixture of two pseudoviruses: one containing the sequence near RdRP gene (NC_045512: 13,242-16,236) and the other containing the full-length sequence of the N gene (NC_045512: 28,274-29,533). The virus preservation solution in (1) was used to dilute each of the pseudovirus to have a copy number concentration of $10^4$ copies/ml.

(4) SARS-CoV-2 negative control:

The negative control is a pseudovirus with internal standard ACTB gene that does not carry a sequence from the SARS-CoV-2 RNA. The RNA copy number concentration in the virus preservation solution was adjusted to $10^4$ copies/ml.

Test Steps

The SARS-CoV-2 PCR amplification reaction lyophilized powder in the kit, SARS-CoV-2 positive control and SARS-CoV-2 negative control were mixed at room temperature and centrifuged at low speed for 10 seconds.

The total number of reactions is determined to be the number of samples to be tested plus two. In other words, if the number of samples is n, then the total number of reactions will be N=n+2.

The sample(s) to be tested (actual SARS-CoV-2 virus in virus preservation solution, 25 μl), 25 μl of SARS-CoV-2 positive quality control and SARS-CoV-2 negative quality control each are added to SARS-CoV-2 PCR amplification reaction lyophilized powder. Seal the membrane tightly or close the cap of the PCR reaction tube, and immediately centrifuge the reaction tube at low speed. The PCR reaction tube is transferred placed in the sample container of the ABI 7500 PCR System, and the sample numbers are recorded. placement order. The reaction parameter window was opened to set the cycle conditions. The reaction program parameters are shown in the following table:

TABLE 8

| Step | Temp. | Time | No. of cycle |
|---|---|---|---|
| Reverse transcription | 55° C. | 1 min | 1 |
| Pre-denaturation | 96° C. | 20 s | 1 |
| Denaturation | 96° C. | 5 s | |
| Annealing, extension and fluorescence detection | 58° C. | 30 s | 40 |

The results are interpreted based on the pattern and Ct value of each fluorescence-cycle number curve. The reporter fluorescence of the ORF1ab gene is FAM, the reporter fluorescence of the N gene is ROX, and the reporter fluorescence of the internal quality control gene is VIC.

Validity Determination:

Only if the following conditions 1), 2), and 3) are satisfied at the same time, the experiment is deemed valid, otherwise it is deemed invalid:

(1) Positive quality control: The FAM and ROX channels have typical S-type amplification curves and Ct values <37; The VIC channel has a typical S-type amplification curve and Ct value <37.

(2) Negative quality control: FAM, ROX channel value Ct>37 or no Ct value, the line is a straight line or a slight slant line, no typical S-type amplification curve. The VIC channel has a typical S-type amplification curve and CT value <37.

(3) Sample to be tested: The VIC channel has a typical S-type amplification curve.

Sample Test Results Determination

After the amplification reaction is completed, the results for the test sample(s) are automatically saved, and the start value, end value, and threshold value of the baseline are adjusted according to the analyzed image. The detection result can be read in the Report window, and interpreted according to the below table.

TABLE 9

| Targets | Channel | Results interpretation |
|---|---|---|
| Open Reading Frame: ORF1ab | FAM | Positive: one or two channels having Ct values <37, the curves take S-shape and noticeable exponential growth phase; |
| Nucleocapsid gene N | ROX | Negative: both channels having Ct values >37 or no Ct value |

SARS-CoV-2 Detection Kits and Fluorescence PCR Amplification

The performance of the viral nucleic acid detection kit of the present disclosure (with test sample, positive control and negative control) was evaluated. 7 samples are used in this procedure, as shown in the below table.

TABLE 10

| Sample No. | Contents |
|---|---|
| 1 | Positive sample diluted 10-fold |
| 2 | Positive sample diluted 20-fold |
| 3 | Positive sample diluted 40-fold |
| 4 | Positive sample diluted 80-fold |
| 5 | Positive sample diluted 160-fold |
| 7 | Positive control |
| 8 | Negative control |

Test procedure: the kit of the present invention does not require a nucleic acid extraction step, and the PCR amplification reaction can be performed immediately after the sample is collected by a pharyngeal swab and stored in the virus preservation solution.

PCR reaction systems preparation: 25 μl of virus preservation solution containing viral sample is added to the PCR amplification lyophilized powder.

PCR amplification conditions are shown in the below table:

TABLE 11

| | | | |
|---|---|---|---|
| Reverse transcription | 55° C. | 1 min | |
| Pre-denaturation | 96° C. | 20 s | |
| Amplification and fluorescence detection | 96° C. | 5 s | 45 cycles |
| | 58° C. | 30 s | |

Test results: the threshold was set to 10000, the baseline was set to 6-15 cycles, and the Ct values are summarized in the below table.

TABLE 12

|  | Sample No. 1 | Sample No. 2 | Sample No. 3 | Sample No. 4 | Sample No. 5 | Positive Control | Negative Control |
| --- | --- | --- | --- | --- | --- | --- | --- |
| FAM (ORF) | 31.34 | 32.68 | 34.23 | 35.75 | 37.49 | 25.65 | N/A |
| VIC | 27.2 | 27.59 | 27.41 | 27.72 | 27.49 | 27.61 | 27.65 |
| ROX (N) | 29.33 | 30.53 | 31.35 | 32.77 | 33.4 | 28.94 | N/A |

The test results show that the kit of the present invention can successfully detect a positive sample diluted 160-fold by performing virus detection according to the direct amplification method.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific formulations, kits and methods and illustrative examples shown and described. Accordingly, departures may be made from such details without departing from the scope or spirit of the general inventive concept.

The invention claimed is:

1. A method of preparing a viral sample comprising an RNA virus for PCR amplification and performing PCR amplification, comprising:
   (a) mixing a viral sample with: (1) a virus preservation solution comprising: bovine serum albumin, fish gelatin, a surfactant, a pH buffer, and wherein the virus preservation solution has a pH in the range of between 8.0 and 8.5 to form a virus preservation mixture, and
   (b) storing and transporting the virus preservation mixture at room temperature without degradation of the RNA of the virus;
   (c) mixing the virus preservation mixture with (2) a nucleic acid amplification reaction preparation in the form of lyophilized powder comprising M-MLV Reverse Transcriptase (MMLV), Taq DNA polymerase, dNTP, primers, and fluorescence probes, to thereby obtain a PCR-sample solution where the concentration of dNTP is between 0.05 mM and 0.5 mM, the concentration of primers is between 0.05 μM and 0.5 the concentration of fluorescence probes is between 0.05 μM and 0.5 μM, the concentration of MMLV is between 1 U/μl and 50 U/μl, and the concentration of Taq DNA polymerase is between 0.1 U/μl and 3 U/μl; and
   (d) performing qPCR amplification reaction on the PCR-sample solution, wherein the amplification reaction is completed within 30 minutes.

2. The method of claim 1, wherein the RNA virus is a coronavirus.

3. The method of claim 1, wherein the coronavirus is SARS-CoV-2 virus.

4. The method of claim 1, wherein the thermocycling conditions for the qPCR include:

reverse transcription reaction: 45° C.-60° C. for 0.5 min-10 min;

thermal denaturation reaction: 94° C.-99° C. for 10 s-60 s; and amplification reaction: 94° C.-99° C. for 1 s-10 s, 55° C.-60° C. for 10 s-45 s for at least 35 cycles.

5. The method of claim 1, wherein the pH buffer of the virus preservation solution comprises Tris-HCl.

6. The method of claim 1, wherein the virus preservation solution further comprises EDTA.

7. The method of claim 1, wherein the virus preservation solution further comprises $NaN_3$.

8. The method of claim 1, wherein the virus preservation solution further comprises DMSO and glycerol.

9. The method of claim 1, wherein the pH buffer of the virus preservation solution comprises Tris-HCl, and in the total amount of the virus preservation solution:

the molar concentration of Tris-HCl is between 10 mM and 200 mM, the weight concentration of bovine serum albumin is between 1 µg/µl and 10 µg/µl, and the weight percentage of fish gelatin is between 0.1% and 2%.

10. The method of claim 9, wherein the virus preservation solution further comprises DMSO and glycerol, and wherein in the total amount of the virus preservation solution:

the volume percentage of DMSO is between 0.1% and 5%, and the volume percentage of glycerol is between 1% and 10%.

11. The method of claim 1, wherein the nucleic acid amplification reaction preparation further comprises one or both of KCl and $MgCl_2$.

12. The method of claim 11, wherein the nucleic acid amplification reaction preparation further comprises polyoxyethylene (20) sorbitan monolaurate.

13. The method of claim 11, wherein the nucleic acid amplification reaction preparation further comprises a pH buffer.

14. The method of claim 1, wherein the nucleic acid amplification reaction preparation further comprises KCl and polyoxyethylene (20) sorbitan monolaurate, and wherein in the total amount of the PCR-sample solution:

the concentration of dNTP is between 0.05 mM and 0.5 mM, the concentration of primers is between 0.05 µM and 0.5, the concentration of fluorescence probes is between 0.05 µM and 0.5 µM, the concentration of MMLV is between 1 U/µl and 50 U/µl, and the concentration of Taq DNA polymerase is between 0.1 U/µl and 3 U/µl.

15. The method of claim 1, wherein the nucleic acid amplification reaction preparation further comprises trehalose, sucrose, and polyoxyethylene (20) sorbitan monolaurate, wherein in the total amount of the PCR-sample solution:

the weight concentration of trehalose is between 1% and 10%, the weight concentration of sucrose is between 1% and 10%, and the weight concentration of polyoxyethylene (20) sorbitan monolaurate is between 0.005% and 0.2%.

16. The method of claim 1, wherein the nucleic acid amplification reaction preparation in the form of lyophilized powder comprises at least one sugar as lyoprotectant.

17. The method of claim 1, the nucleic acid amplification reaction preparation in the form of lyophilized powder further comprises Tris-HCl, potassium chloride, at least one or both of trehalose and sucrose, and optionally PEG6000, polyoxyethylene (20) sorbitan monolaurate.

18. The method of claim 4, wherein the reverse transcription reaction for the qPCR is performed at 55° C.-55° C.

19. The method of claim 4, wherein the reverse transcription reaction for the qPCR is performed for a duration of time of 0.5 min-1 min.

* * * * *